United States Patent
Panyard et al.

(10) Patent No.: US 7,690,260 B2
(45) Date of Patent: Apr. 6, 2010

(54) METHOD AND SYSTEM HAVING ULTRASONIC SENSOR MOVABLE BY TRANSLATION DEVICE FOR ULTRASONIC PROFILING OF WELD SAMPLES

(75) Inventors: James Panyard, Livonia, MI (US);
Timothy Potter, Dearborn, MI (US);
William Charron, Rochester Hills, MI (US); Deborah Hopkins, Berkeley, CA (US); Frederic Reverdy, Paris (FR)

(73) Assignees: Ford Motor Company, Dearborn, MI (US); The Regents of the University of California, Oakland, CA (US)

( * ) Notice: Subject to any disclaimer, the term of this patent is extended or adjusted under 35 U.S.C. 154(b) by 443 days.

(21) Appl. No.: 11/742,852

(22) Filed: May 1, 2007

(65) Prior Publication Data

US 2008/0271537 A1 Nov. 6, 2008

(51) Int. Cl.
*G01N 29/04* (2006.01)
(52) U.S. Cl. .......................... 73/634; 73/629
(58) Field of Classification Search ................ 73/620, 73/629, 633, 634
See application file for complete search history.

(56) References Cited

U.S. PATENT DOCUMENTS

| 4,375,818 | A | * | 3/1983 | Suwaki et al. ............. 600/463 |
| 4,787,247 | A | * | 11/1988 | Wuchinich et al. ............ 73/620 |
| 4,849,601 | A | | 7/1989 | Haefner et al. |
| 4,861,960 | A | | 8/1989 | Haefner et al. |
| 5,920,014 | A | | 7/1999 | Waschkies |
| 6,072,144 | A | | 6/2000 | Perryman |
| 6,297,467 | B1 | | 10/2001 | Maev et al. |
| 6,948,369 | B2 | | 9/2005 | Fleming et al. |
| 2004/0239317 | A1 | | 12/2004 | Goldfine et al. |
| 2005/0017713 | A1 | | 1/2005 | Goldfine et al. |

FOREIGN PATENT DOCUMENTS

| JP | 61140376 | 6/1986 |
| JP | 05133941 | 5/1993 |

* cited by examiner

*Primary Examiner*—John E Chapman
(74) *Attorney, Agent, or Firm*—Raymond L. Coppiellie; Brooks Kushman P.C.

(57) ABSTRACT

A system for ultrasonic profiling of a weld sample includes a carriage movable in opposite first and second directions. An ultrasonic sensor is coupled to the carriage to move over the sample as the carriage moves. An encoder determines the position of the carriage to determine the position of the sensor. A spring is connected at one end of the carriage. Upon the carriage being moved in the first direction toward the spring such that the carriage and the sensor are at a beginning position and the spring is compressed the spring decompresses to push the carriage back along the second direction to move the carriage and the sensor from the beginning position to an ending position. The encoder triggers the sensor to take the ultrasonic measurements of the sample when the sensor is at predetermined positions while the sensor moves over the sample between the beginning and positions.

16 Claims, 2 Drawing Sheets

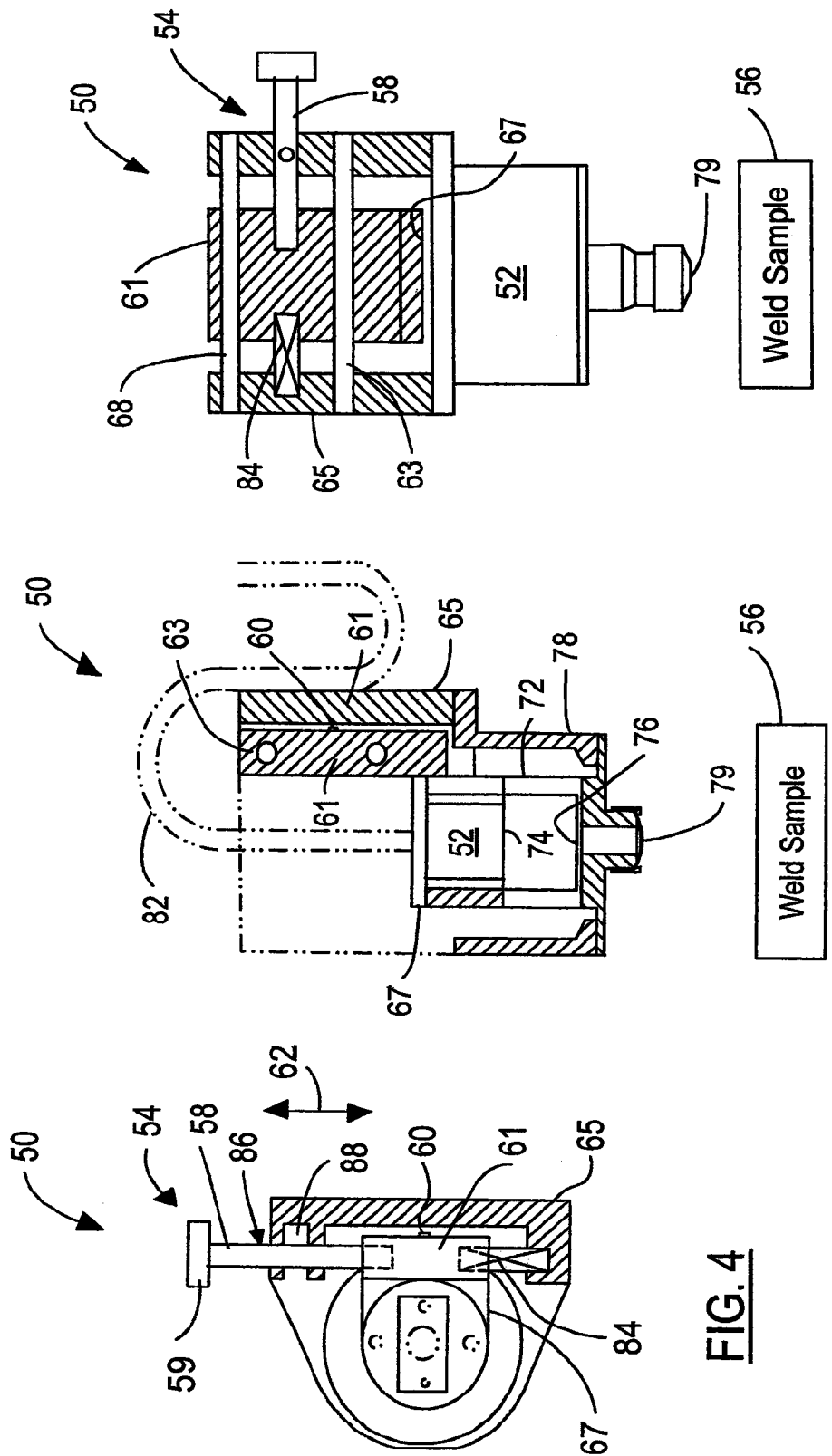

METHOD AND SYSTEM HAVING ULTRASONIC SENSOR MOVABLE BY TRANSLATION DEVICE FOR ULTRASONIC PROFILING OF WELD SAMPLES

STATEMENT REGARDING FEDERALLY SPONSORED RESEARCH OR DEVELOPMENT

The present invention was made with Government support under Contract No. DE-FC05-020R22910 and Contract No. DE-AC02-05CH11231 from the U.S. Department of Energy. The Government has certain rights to the invention.

BACKGROUND OF THE INVENTION

1. Field of the Invention

The present invention relates to ultrasonic profiling of weld samples.

2. Background Art

Resistance spot welds are created by passing current between two welding electrodes on opposite sides of metal sheets being joined. The resistance to electrical current flow at the interface between the sheets causes localized heating that melts the base metal creating a spot weld at the joint. At present, common methods for inspecting spot welds in automotive manufacturing are pry checks and physical tear-downs, during which spot-welded joints are pried apart. The resulting weld buttons are visually inspected or measured with calipers. Although these methods have been used successfully for decades, destructive weld testing has some drawbacks including costs associated with scrap material and the time lag between the onset and identification of problems. In addition, pry tests and tear-downs do not allow personnel to easily collect inspection data that would allow them to identify trends and potential problems. Recent industry studies have demonstrated cost savings associated with implementing non-destructive evaluation (NDE) which derive from finding defects early in the production process and reducing waste compared to destructive testing.

Another problem with destructive inspection techniques is that they are not viable options for lightweight and high-strength materials. Composite structures with adhesive-bonded joints cannot be pry checked, and aluminum is relatively expensive and more difficult to rework than steel making pry checks and tear-downs cost prohibitive. Welds in high-strength steel are often too strong to be pry checked or torn down, and satisfactory welds sometimes fail inter-facially rather than by pulling a weld button, making it difficult for inspectors to distinguish between satisfactory and discrepant welds. Development of NDE techniques is therefore an enabling technology for greater use of lightweight materials in the automotive industry where NDE methods to assure product quality are essential for industry and consumer acceptance of new materials and manufacturing methods.

Ultrasonic weld profiling is a non-destructive testing technique that allows welds to be sized and discrepant welds to be identified. This technique involves measuring the ultrasonic energy transmitted and reflected at the welded interface. Traditional ultrasonic spot-weld inspection systems use conventional high-frequency single-crystal probes working in pulse-echo mode. The output from these mono-probes is a single signal that is an integrated response over an area that depends on the diameter of the probe. Different probes are used for different sized welds. In contrast, a phased array includes many piezoelectric elements that are individually excited by electronic pulses at programmed delay times. As a result, phased arrays have several advantages over conventional ultrasonic probes that derive from the ability to dynamically control the acoustic beam transmitted into the structure under examination. An electronic delay can be applied separately to each electronic channel when emitting and receiving the signal. These delay laws permit constructive and destructive interference of the acoustic wave-front transmitted into the structure, allowing predefined ultrasonic beams to be formed. The acoustic energy can be focused, and delay laws can be used to steer the acoustic beam. Electronic scanning is accomplished by firing successive groups of elements in the array. Electronic scanning combined with mechanical translation of the probe allows several thousands of signals to be measured and analyzed to produce high-resolution two-dimensional images of the welds.

For automotive manufacturing applications, inspection systems have to be robust, light, easy to use, and small enough to permit access to welds in tight corners. A problem with using a motorized mechanical system to move the probe is that it has to be a miniature system meeting size and weight requirements, which increases the initial cost of the probe assembly as well as maintenance and repair costs. A motorized mechanical system is also unattractive because of the high potential for damage or mechanical problems in harsh manufacturing environments. For example, speed irregularities of the motor used for probe translation will cause the weld images generated by the probe to not be accurate as irregularities in motion or variance in speed of the probe is of consequence.

Further, an ultrasonic probe has to be maintained in water as ultrasonic waves do not propagate properly in air. As such, a water path between the probe and the part under inspection has to be maintained. A complication with using a motorized scanning system is that the motor has to be isolated from the water thereby greatly complicating the design of the probe housing. Therefore, a method and system for translation of an ultrasonic probe across a part under inspection which do not require motorized moving parts is desirable.

SUMMARY OF THE INVENTION

The present invention provides a system for ultrasonic profiling of a weld sample. The system includes a translation element movable in opposite first and second directions. A sensor is coupled to the translation element to move over a weld sample as the translation element moves. The sensor is operable to take ultrasonic measurements of the weld sample. An encoder is operable for determining the position of the translation element. The encoder determines the position of the sensor from the position of the translation element. A spring is connected at one end of the translation element. Upon the translation element being moved in the first direction toward the spring such that the translation element and the sensor are at a beginning position relative to the weld sample and the spring is compressed the spring decompresses to push the translation element back along the second direction to move the translation element and the sensor from the beginning position to an ending position relative to the weld sample. The encoder triggers the sensor to take the ultrasonic measurements of the weld sample when the sensor is at predetermined positions relative to the weld sample while the sensor moves over the weld sample from the beginning position to the ending position.

The present invention provides a method for ultrasonic profiling of a weld sample. The method includes placing a carriage movable in opposite first and second directions at a center position relative to a weld sample. A sensor is coupled to the carriage to move as the carriage moves. The method includes pushing the carriage from the center position in the first direction toward a spring connected at one end of the carriage such that the spring is compressed and the carriage and the sensor are at a beginning position relative to the weld sample. The method includes allowing the spring to decompress to push the carriage back along the second direction to move the carriage and the sensor from the beginning position to an ending position relative to the weld sample. The method includes monitoring the position of the carriage using an encoder to determine the position of the sensor. The method includes triggering the sensor to take ultrasonic measurements of the weld sample when the sensor is at predetermined positions relative to the weld sample while the sensor moves over the weld sample from the beginning position to the ending position.

BRIEF DESCRIPTION OF THE DRAWINGS

Features of the present invention which are believed to be novel are set forth with particularity in the appended claims. The present invention, both as to its organization and manner of operation, together with further objects and advantages thereof, may be best understood with reference to the following description, taken in connection with the accompanying drawings in which:

FIG. 4 illustrates a top cross-sectional view of a system having an ultrasonic sensor movable by a translation device for ultrasonic profiling of a weld sample in accordance with a preferred embodiment of the present invention;

FIG. 5 illustrates a side cross-sectional view of the system shown in FIG. 4; and FIG. 6 illustrates a frontal cross-sectional view of the system shown in FIG. 4.

DETAILED DESCRIPTION OF THE PREFERRED EMBODIMENT(S)

Figure 1:
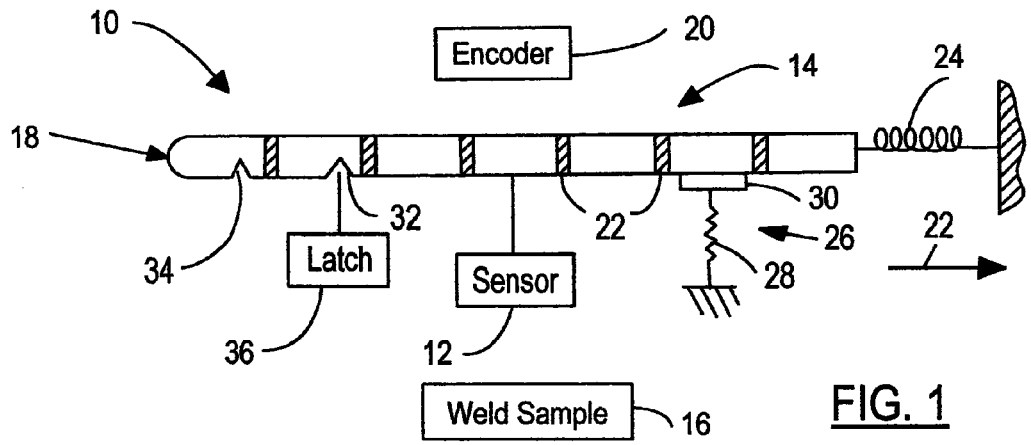
FIG. 1 illustrates a block diagram of a system having an ultrasonic sensor movable by a translation device for ultrasonic profiling of a weld sample in accordance with an embodiment of the present invention in which the translation device is at a center position relative to the weld sample.
Figure 2:
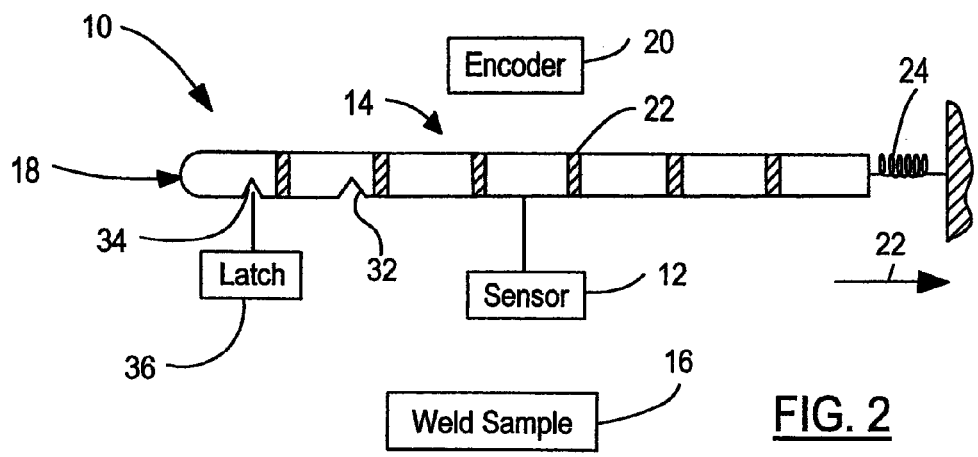
FIG. 2 illustrates a block diagram of the system in which the translation device is at a first end-of-travel position relative to the weld sample such that the sensor is at a beginning position for ultrasonic profiling of the weld sample.
Figure 3:
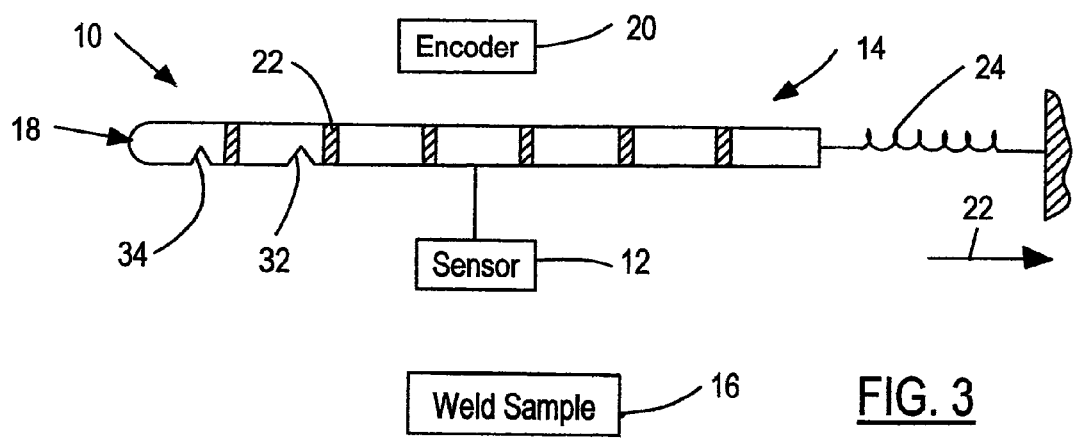
FIG. 3 illustrates a block diagram of the system in which the translation device is at a second end-of-travel position, opposite to the first end-of-travel position, relative to the weld sample such that the sensor is at an ending position for ultrasonic profiling of the weld sample.

Referring now to FIGS. 1, 2, and 3, block diagrams of a system 10 having an ultrasonic sensor(s) 12 movable by a translation device 14 for ultrasonic profiling of a weld sample 16 (i.e., weld nugget) in accordance with an embodiment of the present invention are shown. FIG. 1 illustrates translation device 14 at a center position relative to weld sample 16. FIG. 2 illustrates translation device 14 at a first end-of-travel position relative to weld sample 16 such that sensor 12 is at a beginning position for ultrasonic profiling of the sample. FIG. 3 illustrates translation device 14 at a second end-of-travel position, opposite to the first end-of-travel position, relative to weld sample 16 such that sensor 12 is at an ending position for ultrasonic profiling of the sample.

Translation device 14 includes a shaft 18. Shaft 18 is movable relative to weld sample 16 in the "x" direction indicated by reference numeral 22 and in the direction opposite to the "x" direction. Sensor 12 is attached to shaft 18 such that the sensor moves as the shaft moves. Thus, sensor 12 moves over (i.e., across) weld sample 16 as shaft 18 moves in a direction parallel to "x" direction 22.

An optical encoder 20 is fixed in position and faces a relatively small portion of shaft 18 as the shaft moves. A code strip 22 is on a surface of shaft 18 facing encoder 20. Code strip 22 includes markings indicative of respective portions of shaft 18 along the length of the shaft parallel to "x" direction 22. Encoder 20 transmits optic signals toward the portion of shaft 18 facing the encoder during the movement of the shaft, and receives optic signals reflected by the markings of the associated portion of code strip 22. In this way, encoder 20 can determine the "x" position of shaft 18 from the reflected optic signals and can therefore determine the "x" position of sensor 12 relative to weld sample 16 as the sensor moves in response to shaft movement.

In operation for ultrasonic profiling of weld sample 16, translation device 14 moves sensor 12 across weld sample while triggering the sensor to take ultrasonic readings at predetermined "x" positions of weld sample 16. Sensor 12 does not physically contact weld sample 16 and moves over the sample while moving across the sample. Sensor 12 is triggered to transmit ultrasonic energy toward weld sample 16 and measure ultrasonic energy reflected by the sample as the sensor moves over the sample. In this way, sensor 12 generates a profile of weld sample 16 indicative of the internal structure of the sample (i.e., indicative of the internal weld nugget structure). The profile is generally a measurement of the amplitude of the reflected ultrasonic energy as a function of each "x" position of weld sample 16.

Sensor 12 is triggered to transmit ultrasonic energy bursts at predetermined "x" positions of weld sample 16 and measure reflected ultrasonic energy at the predetermined "x" positions of the sample as the sensor moves across the sample. Alternatively, sensor 12 continuously transmits an ultrasonic energy burst and is triggered to measure reflected ultrasonic energy at the predetermined "x" positions of weld sample 16 as the sensor moves across the sample.

Encoder 20 acts as the triggering element of sensor 12 for the acquisition of the profile data of weld sample 16. That is, encoder 20 triggers the ultrasonic energy measurements (i.e., readings) of sensor 12 to be taken at the predetermined "x" positions of weld sample 16 by monitoring the "x" position of shaft 18 as the shaft (and the sensor) moves relative to the sample. Each "x" position of shaft 18 (and sensor 12) corresponds to a respective "x" position of weld sample 16. Encoder 20 determines the "x" position of shaft 18 (and sensor 12) in conjunction with the use of code strip 22. When shaft 18 moves to each predetermined "x" position, encoder 20 triggers sensor 12 to take ultrasonic energy measurements. As such, triggering is done at positions of shaft 18 (and sensor 12) determined by encoder 20 with the use of code strip 22. Consequently, any variance in speed or irregularities in motion of shaft 18 as the shaft moves sensor 12 across weld sample 16 is of no consequence for the ultrasonic profiling of the sample.

By the use of encoder 20 with code strip 22 for triggering sensor 12 to take sensor readings when the sensor is at the predetermined positions, the sensor collects measurement data at precise position intervals to accurately represent the profile of weld sample 16. Using encoder 20 with code strip 22 to trigger ultrasonic readings of sensor 12 (along with relatively simple non-motorized actuation of shaft 18 to move the sensor relative to weld sample 16 as described in further detail below) eliminates the motor and controller configuration of traditional ultrasonic sensor systems.

As described above, sensor 12 moves over weld sample 16 as shaft 18 moves to generate an ultrasonic profile of the sample. As such, shaft 18 moves relative to weld sample 16 and encoder 20 as both the sample and the encoder are fixed in position during the profiling. As code strip 22 is fixed to shaft 18, the code strip moves relative to encoder 20 as the shaft moves. Encoder 20 triggers sensor 12 as code strip 22 moves relative to the encoder. That is, encoder 20 triggers sensor 12 when code strip 22 indicates that shaft 18 (and the sensor) is at the predetermined "X" positions. As a result, regardless of fast, slow, or variable movement of shaft 18 (and sensor 12) across weld sample 16, encoder 20 triggers the sensor to take ultrasonic energy measurements at prescribed position intervals. In turn, sensor 12 produces an accurate profile of weld sample 16.

Sensor 12 may include a plurality of sensor elements such that the sensor is a sensor array. As an example, the sensor array is an ultrasonic sensor phased array ("USPA") in which the sensor elements are aligned in the "y" direction next to one another. Each sensor element (i.e., each sensor 12) takes its own ultrasonic readings of weld sample 16 as the sensor array is moved in the "x" direction over the sample. In this way, the profile of weld sample 16 generated by the sensor array takes into account both "x" and "y" dimensions of the sample as each measurement is respectively associated with an "x" and "y" position pair of the sample.

In an embodiment in which sensor 12 is a sensor array, the sensor elements of the sensor array are arranged in a linear series such that they are 2.5 mm apart from each neighboring sensor element. As the sensor array is linearly moved over weld sample 16 at 2.5 mm intervals, the sensor elements produce a grid profile of the sample. With the sensor elements at a 2.5 mm spacing and the markings of code strip 22 spaced apart from one another by 2.5 mm, the sensor elements produce an accurate representation (i.e., profile) of weld sample 16 in a uniform grid.

A spring 24 provides for the non-motorized actuation of shaft 18 to move sensor 12 relative to weld sample 16. Spring 24 is connected at an end to one end of shaft 18 (i.e., the spring is connected to the right-hand side end of the shaft as shown in FIGS. 1, 2, and 3). The other end of spring 24 is fixed in position. Spring 24 applies biasing forces to shaft 18 in a direction parallel to "x" direction 22. The bias force of spring 24 acts on shaft 18 in a direction opposite to "x" direction 22 upon the shaft 18 being linearly pushed in the "x" direction toward the spring. As such, after shaft 18 is pushed inward toward spring 24 (as shown in FIG. 2), the spring biases the shaft in the direction opposite to "x" direction 22 upon the initial pushing force being removed. The biasing force of spring 24 on shaft 18 causes the shaft to move, backward from the initial inward movement, in the direction opposite to "x" direction 22 (as shown in FIG. 3). The speed of movement of shaft 18 due to spring 24 depends upon the amount of biasing force applied by the spring.

A drag element 26 controls the speed of translation ("X" movement) of shaft 18 caused by spring 24 by acting as a damper to the biasing force of the spring. Drag element 26 includes a drag spring 28 and a drag member 30. Drag spring 28 is connected at an end to one end of drag member 30 and is fixed at its other end. Drag spring 28 applies a biasing force to drag member 30. Drag member 30 is configured to circumferentially engage a surface portion of shaft 18 at a respective "x" portion of the shaft. The biasing force of drag spring 28 is generally perpendicular to the biasing force of spring 24. Drag member 30 applies the biasing force of drag spring 28 onto shaft 18 thereby hindering "x" movement of the shaft. As such, drag element 26 inhibits relatively rapid movement of shaft 18 (and sensor 12) across weld sample 16.

Shaft 18 includes first and second detents 32, 34. Detents 32, 34 are generally at the end of shaft 18 opposite to the end of the shaft connected to spring 24 (i.e., the detents are at the left-hand side end of the shaft as shown in FIGS. 1, 2, and 3). Detents 32, 34 are cut into a portion of the circumferential surface of shaft 18.

A latch mechanism 36 engages one of detents 32, 34 at a time to set shaft 18 in a respective one of two positions. Particularly, latch mechanism 36 engages first detent 32 to set shaft 18 in the center position relative to weld sample 16 as shown in FIG. 1. Likewise, latch mechanism 36 engages second detent 34 to set shaft 18 at the first end-of-travel position relative to weld sample 16 as shown in FIG. 2.

In operation, an operator moves translation device 14 to place shaft 18 and sensor 12 a center position over weld sample 16 as shown in FIG. 1. Latch mechanism 36 engages first detent 32 to temporarily lock shaft 18 (and sensor 12) at the center position relative to weld sample 16. The operator then pushes shaft 18 inward in "x" direction 22 toward spring 24 to place the shaft (and sensor 12) at the beginning position corresponding to the first end-of-travel position of the shaft (and the sensor) over weld sample 16 as shown in FIG. 2. During this inward movement of shaft 18, latch mechanism 36 disengages from first detent 32 and engages second detent 34 to temporarily lock the shaft (and sensor 12) at the beginning position relative to weld sample 16.

At this point, encoder 20 sends a signal to a processor or the like that it is ready to begin ultrasonic data collection of weld sample 16. Shaft 18 is then circumferentially rotated by 90 degrees or so causing latch mechanism 36 to disengage from second detent 34. This disengagement allows the biasing force of spring 24 on shaft 18 to move the shaft backward in a direction opposite to "x" direction 22. The biasing force of spring 24 causes shaft 18 to move in the direction opposite to "x" direction 22 until the shaft (and sensor 12) reaches an ending position at an opposite second end-of-travel position as shown in FIG. 3. During this movement of shaft 18, encoder 20 monitors the position of the shaft (and sensor 12) to trigger the sensor to take ultrasonic measurements of weld sample 16. As described above, each ultrasonic measurement corresponds to a predetermined "x" position of weld sample 16.

Because speed is not critical, the interval of ultrasonic data collection can be precise. When sensor 12 reaches the ending position, encoder 20 signals an end of the ultrasonic data collection. At this point, shaft 18 is returned to the center position until first detent 32 is felt. This is the start of another ultrasonic profile cycle.

As such, spring 24 is used to initiate motion of shaft 18 for the purpose of moving sensor 12 over weld sample 16 to take ultrasonic measurements of the sample. No motors or controllers are required for the movement of shaft 18 or for the triggering of sensor 12. The speed of translation (i.e., movement of shaft 18 from the beginning position to the ending position) of the shaft is determined by drag element 26 in conjunction with spring 24.

FIG. 1 illustrates a block diagram of system 10 in which translation device 14 is in the center position relative to weld sample 16. As shown, latch mechanism 36 is engaged with first detent 32 to temporarily lock shaft 18 (and sensor 12) in the center position relative to weld sample 16. The center position corresponds to the mean position of weld sample 16 (i.e., the center of the sample).

FIG. 2 illustrates a block diagram of system 10 in which translation device 14 is pushed in "x" direction 22 into the beginning position corresponding to the first end-of-travel position of shaft 18 (and sensor 12) relative to weld sample 16. As shown, shaft 18 is moved inward toward spring 24 and the spring is compressed. Latch mechanism 36 is engaged with second detent 34 to temporarily lock shaft 18 (and sensor 12) in the beginning position relative to weld sample 16.

FIG. 3 illustrates a block diagram of system 10 in which translation device 14 has moved in the direction opposite to "x" direction 22 from the first end-of-travel position to the ending position corresponding to the opposite second end-of-travel position. As shown, shaft 18 moves backward away from spring 24. The movement of shaft 18 is a result of the biasing force of spring 24 acting on the shaft after latch mechanism 36 has been disengaged from second detent 34.

Referring now to FIGS. 4, 5, and 6, with continual reference to FIGS. 1, 2, and 3, different views of a system 50 having an ultrasonic sensor 52 movable by a translation device 54 for ultrasonic profiling of a weld sample 56 in accordance with a preferred embodiment of the present invention are shown. FIG. 4 illustrates a top cross-sectional view of system 50. FIG. 5 illustrates a side cross-sectional view of system 50. FIG. 6 illustrates a front cross-sectional view of system 50.

Translation device 54 generally includes a shaft 58, an optical encoder 60, a movable carriage 61, and a fixed C-frame 65. Shaft 58 includes a hand knob 59 at one end. Shaft 58 rotates in response to an operator turning hand knob 59. Shaft 58 extends through a "c" end of C-frame 65, which is fixed in position, and attaches to one end of carriage 61. Carriage 61 is between the "c" ends of c-frame 65. A pair of linear bearings 63, spaced apart from one another and running parallel to one another, extend through carriage 61 and are respectively fixed at their ends to the "c" ends of c-frame 65.

Shaft 58 is linearly movable in both directions parallel to direction 62 to move relative to weld sample 56. Carriage 61 linearly moves along linear bearings 63 in either of directions 62 as shaft 58 moves. Carriage 61 includes a sensor mount 67 at its lower end. Sensor mount 67 includes a cable 82 which communicates ultrasonic data from sensor 52 to a processor and communicates triggering data from encoder 60 to sensor 52 via the processor. Sensor 52 is attached to sensor mount 67 such that the sensor moves as carriage 61 moves in response to shaft 58 moving. Thus, sensor 52 moves over weld sample 56 as carriage 61 moves in either of directions 62. Encoder 60 is fixed in position on carriage 61 and faces a relatively small portion of the main body of c-frame 65.

A code strip is on a surface of the main body of c-frame 65. The code strip includes markings indicative of respective portions of the main body of c-frame 65 along the length of the main body of the c-frame. Encoder 60 transmits optic signals toward the portion of the main body of c-frame 65 facing the encoder during the movement of carriage 61, and receives optic signals reflected by the markings of the associated portion of the code strip. In this way, encoder 60 determines the position of carriage 61 from the reflected optic signals and therefore determines the position of sensor 52 relative to weld sample 56 as the sensor moves in response to carriage movement.

A barrel 78 is fixed to a lower portion of c-frame 65. A fluid chamber 72 is positioned within barrel 78. Fluid chamber 72 includes an upper seal ring 74 and a lower plate 76. Sensor 52 is suspended within fluid chamber 72 such that sensor is positioned between sensor mount 67 and lower plate 76. As such, sensor 52 and fluid chamber 72 move together as shaft 58 and carriage 61 move.

Fluid chamber 72 includes an aqueous fluid which aids in the transmission of the ultrasonic waves between sensor 52 and weld sample 56. The close coupling between sensor 52 and weld sample 56 is done through the aqueous fluid within fluid chamber 72. No physical contact between sensor 52 and weld sample 56 exists as the sensor performs ultrasonic profiling of the sample when translation device 54 is placed over the sample. The contact surface is a membrane 79 having the same density as water. Membrane 79 is at the far bottom of the device and contacts weld sample 56. Sensor 52 is suspended within fluid chamber 72 over membrane 79. The aqueous fluid within fluid chamber 72 surrounds sensor 52 and extends down into the cylindrical area at the bottom of the device and is contained by membrane 79. Membrane 79 is in contact with weld sample 56. As described above, as sensor 52 moves over weld sample 56, the sensor takes ultrasonic readings of the sample. The readings are taken at regular intervals based on the marking intervals of the code strip on the main body of c-frame 65.

Again, encoder 60 acts as the triggering element of sensor 52 for the acquisition of the profile data of weld sample 56. That is, encoder 60 triggers the ultrasonic energy measurements (i.e., readings) of sensor 52 to be taken at the predetermined positions of weld sample 56 by monitoring the position of sensor 52 as the sensor moves relative to the sample. Each position of sensor 52 corresponds to a respective position of weld sample 56. Encoder 60 determines the position of sensor 52 in conjunction with the use of the code strip on the main body of c-frame 65. When sensor 52 moves through each predetermined position, encoder 60 triggers the sensor to take ultrasonic energy measurements. As such, triggering is done at positions of sensor 52 determined by encoder 60 with the use of the code strip.

Sensor 52 may include a plurality of sensor elements such that the sensor is a sensor array. Each sensor element takes its own ultrasonic readings of weld sample 56 as the sensor array is moved over the sample. In this way, the profile of weld sample 56 generated by the sensor array takes into account both "x" and "y" dimensions of the sample as each measurement is respectively associated with an "x" and "y" position pair of the sample.

A spring 84 is connected at an end to carriage 61 and the other end of spring 84 is fixed to an end of c-frame 65. Spring 84 applies biasing forces to carriage 61 in directions 62. The bias force of spring 84 acts on carriage 61 in direction away from the end of c-frame 65 upon carriage 61 being pushed toward spring 84 in response to inward pushing movement of shaft 58. As such, after carriage 61 is pushed inward toward spring 84, spring 84 biases carriage 61 in the opposite direction upon the initial pushing force being removed. The biasing force of spring 84 on carriage 61 causes the carriage to move along linear bearings 63 along with shaft 58, backward from the initial inward movement, in the opposite direction. The speed of movement of carriage 61 due to spring 84 depends upon the amount of biasing force applied by spring 84.

Translation device 54 may further include a drag element having a drag spring and a drag member. The drag spring is connected at an end to one end of the drag member and is fixed to c-frame 65 at its other end. The drag spring applies a biasing force to the drag member. The drag member is configured to circumferentially engage a surface portion of shaft 58 at a respective portion of the shaft. The biasing force of the drag spring is generally perpendicular to the biasing force of spring 84. The drag member applies the biasing force of the drag spring onto shaft 58 thereby hindering movement of the shaft (and carriage 61 and sensor 58).

Shaft 58 includes first and second detents (generally designated as reference numeral 86). The detents are generally at the end of shaft 58 opposite to the end of shaft 58 connected to carriage 61. The detents are cut into a portion of the circumferential surface of shaft 58.

Translation device 54 further includes a latch mechanism (generally designated as reference numeral 88). The latch mechanism engages one of the detents at a time to set shaft 58 in a respective one of two positions. Particularly, the latch mechanism engages the first detent to set shaft 58 in a center position relative to weld sample 56. Likewise, the latch mechanism engages the second detent to set shaft 58 in at a first end-of-travel position relative to weld sample 56.

In operation, an operator moves shaft 58 to place sensor 52 a center position over weld sample 56. The latch mechanism then engages the first detent to temporarily lock shaft 58 (and carriage 61 and sensor 52) at the center position relative to weld sample 56. The operator then pushes shaft 58 inward toward spring 84 to place the shaft (and carriage 61 and sensor 52) at a beginning position corresponding to a first end-of-travel position of the shaft (and the sensor) over weld sample 56. During this inward movement of shaft 58, the latch mechanism disengages from the first detent and engages the second detent to temporarily lock the shaft (and carriage 61 and sensor 52) at the beginning position relative to weld sample 56.

Shaft 58 is then circumferentially rotated by 90 degrees or so causing the latch mechanism to disengage from the second detent. Upon this disengagement, spring 84 applies a biasing force on carriage 61 causing the carriage and shaft 58 to move outward in an opposite direction. The biasing force of spring 84 causes carriage 61 to move in the opposite direction until shaft 58 (and carriage 61 and sensor 52) reaches an ending position at an opposite second end-of-travel position. During this movement, encoder 60 monitors the position of carriage 61 (and sensor 52) to trigger the sensor to take the ultrasonic measurements of weld sample 56.

As such, spring 84 is used to initiate motion of carriage 61 and shaft 58 for the purpose of moving sensor 52 over weld sample 56 to take ultrasonic measurements of the sample.

While the best mode for carrying out the present invention has been described in detail, those familiar with the art to which this present invention relates will recognize various alternative designs and embodiments for practicing the present invention as defined by the following claims.

What is claimed:

1. A system for ultrasonic profiling of a weld sample, the system comprising:
   a translation element movable in opposite first and second directions;
   a sensor coupled to the translation element to move over a weld sample as the translation element moves, wherein the sensor is operable to take ultrasonic measurements of the weld sample;
   an encoder operable for determining the position of the translation element, wherein the encoder determines the position of the sensor from the position of the translation element; and
   a spring connected at one end of the translation element, wherein upon the translation element being moved in the first direction toward the spring such that the translation element and the sensor are at a beginning position relative to the weld sample and the spring is compressed the spring decompresses to push the translation element back along the second direction to move the translation element and the sensor from the beginning position to an ending position relative to the weld sample;
   wherein the encoder triggers the sensor to take the ultrasonic measurements of the weld sample when the sensor is at predetermined positions relative to the weld sample while the sensor moves over the weld sample from the beginning position to the ending position;
   wherein the translation element includes a shaft and a carriage both movable in the first and second directions, wherein the shaft is connected at one end to a first end of the carriage, wherein the spring is connected at one end to a second end of the carriage, wherein the sensor is coupled to the carriage to move as the carriage moves.

2. The system of claim 1 further comprising:
   a damper assembly pressed against a portion of the shaft to slow movement of the shaft and the sensor as the shaft and the sensor move from the beginning position to the ending position in response to decompression of the spring.

3. The system of claim 1 wherein:
   the encoder is an optical encoder.

4. The system of claim 3 wherein:
   the optical encoder determines the position of the shaft from a code strip of markings.

5. The system of claim 1 further comprising:
   a fixed c-frame, wherein the spring is connected between one end of the c-frame and the spring, wherein the shaft extends through the other end of the c-frame.

6. The system of claim 1 wherein:
   the sensor is placed within a chamber within a barrel coupled to the translation element, wherein the chamber is filled with aqueous fluid.

7. The system of claim 1 wherein:
   the ultrasonic measurements of the weld sample taken by the sensor are indicative of the internal structure of a weld nugget of the weld sample.

8. The system of claim 1 wherein:
   the sensor includes an array of sensor elements.

9. A system for ultrasonic profiling of a weld sample, the system comprising:
   a translation element movable in opposite first and second directions;
   a sensor coupled to the translation element to move over a weld sample as the translation element moves, wherein the sensor is operable to take ultrasonic measurements of the weld sample;
   an encoder operable for determining the position of the translation element, wherein the encoder determines the position of the sensor from the position of the translation element; and
   a spring connected at one end of the translation element, wherein upon the translation element being moved in the first direction toward the spring such that the translation element and the sensor are at a beginning position relative to the weld sample and the spring is compressed the spring decompresses to push the translation element back along the second direction to move the translation element and the sensor from the beginning position to an ending position relative to the weld sample;
   wherein the encoder triggers the sensor to take the ultrasonic measurements of the weld sample when the sensor is at predetermined positions relative to the weld sample while the sensor moves over the weld sample from the beginning position to the ending position;
   wherein the translation element is a shaft, the shaft includes first and second detents;
   the system further comprising a latch, wherein the latch engages the first detent when the shaft and the sensor are placed at a center position between the beginning position and the ending position to temporarily lock the shaft and the sensor at the center position, wherein the latch disengages from the first detent and engages the second detent when the shaft is moved in the first direction toward the spring such that the shaft and the sensor are at the beginning position to temporarily lock the shaft and the sensor at the beginning position.

10. The system of claim 9 wherein:

the latch disengages from the second detent upon the shaft being rotated to enable the spring to decompress and push the shaft back along the second direction to move the shaft and the sensor from the beginning position to the ending position.

11. A method for ultrasonic profiling of a weld sample, the method comprising:

placing a carriage movable in opposite first and second directions at a center position relative to a weld sample, wherein a sensor is coupled to the carriage to move as the carriage moves;

locking the carriage in place at the center position;

unlocking the carriage from the center position to allow the carriage to be pushed from the center position in the first direction toward the spring;

pushing the carriage from the center position in the first direction toward a spring connected at one end of the carriage such that the spring is compressed and the carriage and the sensor are at a beginning position relative to the weld sample;

allowing the spring to decompress to push the carriage back along the second direction to move the carriage and the sensor from the beginning position to an ending position relative to the weld sample;

monitoring the position of the carriage using an encoder to determine the position of the sensor; and triggering the sensor to take ultrasonic measurements of the weld sample when the sensor is at predetermined positions relative to the weld sample while the sensor moves over the weld sample from the beginning position to the ending position.

12. The method of claim 11 further comprising:

locking the carriage in place at the beginning position; and unlocking the carriage from the beginning position to allow the spring to decompress.

13. The method of claim 11 wherein:

the encoder is an optical encoder.

14. The method of claim 11 further comprising:

generating a profile of the weld sample from the ultrasonic measurements taken by the sensor, wherein the profile is indicative of the internal structure of a weld nugget of the weld sample.

15. The method of claim 11 further comprising:

damping the movement of the carriage along the second direction from the beginning position to the ending position.

16. The method of claim 11 wherein:

monitoring the position of the carriage using an encoder includes monitoring code strip markings on the carriage using the encoder.

* * * * *